United States Patent [19]

Okada et al.

[11] Patent Number: 5,762,904
[45] Date of Patent: Jun. 9, 1998

[54] ORAL DELIVERY OF VACCINES USING POLYMERIZED LIPOSOMES

[75] Inventors: Junichi Okada, Yokohama, Japan; Smadar Cohen, Petah Tikva, Israel; Robert S. Langer, Newton, Mass.

[73] Assignee: Massachusetts Institute of Technology, Cambridge, Mass.

[21] Appl. No.: 786,617

[22] Filed: Jan. 17, 1997

Related U.S. Application Data

[63] Continuation of Ser. No. 96,689, Jul. 23, 1993, abandoned.

[51] Int. Cl.⁶ .................... A61K 9/127; A61K 39/00; A61M 36/12
[52] U.S. Cl. .................... 424/1.21; 264/4.1; 264/4.3; 424/9.321; 424/9.4; 424/9.51; 424/9.6; 424/184.1; 424/278.1; 424/450; 424/812; 428/402.2
[58] Field of Search .................... 424/450, 1.21, 424/9.321, 9.51, 184.1, 812, 278.1, 9.4, 9.6; 428/402.2; 264/4.1, 4.3

[56] References Cited

U.S. PATENT DOCUMENTS

| | | | |
|---|---|---|---|
| 4,201,767 | 5/1980 | Fullerton et al. | 424/450 |
| 4,229,360 | 10/1980 | Schneider et al. | |
| 4,348,329 | 9/1982 | Chapman | 554/80 |
| 4,429,008 | 1/1984 | Martin et al. | 428/402.2 |
| 4,485,045 | 11/1984 | Regen | 264/4.6 X |
| 4,522,811 | 6/1985 | Eppstein et al. | 514/2 |
| 4,544,545 | 10/1985 | Ryan et al. | 424/1.21 |
| 4,560,599 | 12/1985 | Regen | 428/36 |
| 4,564,475 | 1/1986 | Masaichiro | 554/3 |
| 4,587,055 | 5/1986 | Regen | 560/205 |
| 4,594,193 | 6/1986 | Regen | 554/81 |
| 4,652,257 | 3/1987 | Chang | 602/52 |
| 4,728,575 | 3/1988 | Gamble et al. | 428/402.2 |
| 4,753,788 | 6/1988 | Gamble | 264/4.1 X |
| 4,808,480 | 2/1989 | Regen | 428/402.2 |
| 4,839,175 | 6/1989 | Guo et al. | 424/450 |
| 4,847,080 | 7/1989 | Neurath et al. | 530/324 |
| 4,861,521 | 8/1989 | Suzuki et al. | 554/80 |
| 4,877,501 | 10/1989 | Schnur et al. | 204/157.64 |
| 4,877,619 | 10/1989 | Richer | 424/450 |
| 4,880,635 | 11/1989 | Janoff et al. | 424/450 |
| 4,900,556 | 2/1990 | Wheatley et al. | 424/450 |
| 4,933,114 | 6/1990 | O'Brien et al. | 554/80 |
| 4,935,171 | 6/1990 | Bracken | 264/4.6 |
| 4,975,282 | 12/1990 | Cullis et al. | 424/450 |
| 4,976,968 | 12/1990 | Steiner et al. | 424/491 |
| 4,990,291 | 2/1991 | Schoen et al. | 264/4.7 |
| 5,004,566 | 4/1991 | Schnur et al. | 554/80 |
| 5,026,557 | 6/1991 | Estis et al. | 424/450 |
| 5,061,484 | 10/1991 | Heldebrant | 424/450 |
| 5,104,736 | 4/1992 | Wallach | 428/402.2 |
| 5,106,740 | 4/1992 | Hasegawa et al. | 424/450 |
| 5,158,769 | 10/1992 | Neurath et al. | 424/189.1 |
| 5,160,740 | 11/1992 | Hasegawa et al. | 424/450 |
| 5,198,224 | 3/1993 | Ono et al. | 424/450 |
| 5,204,096 | 4/1993 | Neurath et al. | 530/350 X |
| 5,230,899 | 7/1993 | Park et al. | 424/450 |
| 5,258,499 | 11/1993 | Konigsberg et al. | 530/351 |
| 5,312,620 | 5/1994 | Ribi | 424/450 X |
| 5,366,881 | 11/1994 | Singh et al. | 435/177 |
| 5,382,435 | 1/1995 | Geary et al. | 424/489 |
| 5,425,993 | 6/1995 | Morancais et al. | 428/402.24 |
| 5,505,967 | 4/1996 | Geary et al. | 424/497 |
| 5,536,490 | 7/1996 | Klaveness et al. | 424/9.51 X |
| 5,679,355 | 10/1997 | Alexander et al. | 424/278.1 |

FOREIGN PATENT DOCUMENTS

| | | |
|---|---|---|
| 0333523 | of 0000 | European Pat. Off. |
| 0333523 | 9/1989 | European Pat. Off. |
| 60-081192 | 5/1985 | Japan |
| WO/GB85/00114 | 3/1985 | WIPO |
| US90/06430 | 11/1990 | WIPO |
| US90/06433 | 11/1990 | WIPO |
| WO 90/06430 | 11/1990 | WIPO |
| WO 90/06433 | 11/1990 | WIPO |
| WO 92/04009 | 3/1992 | WIPO |
| WO 93/10763 | 6/1993 | WIPO |
| WO 95/03035 | 2/1995 | WIPO |
| WO 95/04524 | 2/1995 | WIPO |
| WO 96/13250 | 5/1996 | WIPO |

OTHER PUBLICATIONS

Patel, et al., "Oral Administration of Insulin by Encapsulation within Liposomes", *FEBS Letters*, 62(1):60–63 (1976).

Skoza, F. Jr., et al., "Procedure for Preparation of Liposomes with Large Internal Aqueous Space and High Capture by Reverse–phase Evaporation", *Proc. Natl. Acad. Sci. USA*, 75(9):4194–4198 (1978).

Arrieta–Molero, J.F. et al., 1982, "Orally Administered Liposome–Entrapped Insulin in Diabetic Animals", *Hormone Res.* 16(4):249–256.

Axt, J. et al., 1983, "Biopharmazeutische Untersuchungen an Phospholipid–Liposomen als Trager zur oralen Applikation von Insulin", *Pharmazie* 38(4):249–248.

Choi et al., 1992, "pH–Sensitive Liposomes Containing Polymerized Phosphatidylethanolamine and Fatty Acid", *J. Biochem.* 112:694–699.

(List continued on next page.)

*Primary Examiner*—Richard D. Lovering
*Attorney, Agent, or Firm*—Pennie & Edmonds LLP

[57] ABSTRACT

Polymerized liposomes, methods of preparing the polymerized liposomes and incorporating biologically active substances within the polymerized liposomes, and methods of administering polymerized liposomes containing a biologically active substance to be delivered to a patient are disclosed. The polymerized liposomes are prepared by polymerizing double bond-containing liposomes. The polymerization can be initiated with a source of radiation and/or a free radical initiator. Biologically active substances can be incorporated into both the hydrophilic and hydrophobic layers of the liposomes, either during or after polymerization. The polymerized liposomes can be administered orally to a patient in need of the biologically active substance to be delivered. Examples demonstrate enhanced stability.

13 Claims, 4 Drawing Sheets

OTHER PUBLICATIONS

Dapergolas et al., Oct. 16, 1976, "Hypoglycaemic Effect of Liposome–Entrapped Insulin Administered Intragastrically into Rats", The Lancet 824–827.

Das, N. et al., 1988, "Oral Application of Insulin Encapsulated Liposomes", Biochem. Inter. 16(6):983–989.

Hasegawa et al., 1992, "Mutual Recognition Between Polymerized Liposomes", Biotech. and Applied Biochem. 15:40–47.

Hub et al., 1980, "Polymerizable Phospholipid Analogues New Stable Biomembrane and Cell Models", Agnew Che. Int. Ed. Engi. 11:938.

Manosroi, A. & Bauer, K.H., 1990, "Effects of Gastrointestinal Administration of Human Insulin and a Human–DEAE–Dextran Complex Entrapped in Different Compound Liposomes on Blood Glucose in Rats", Drug Dev. and Indus. Pharm. 16(9):1521–1538.

Patel et al., 1977, "Orally Administered Liposomally Entrapped Insulin" Biochemical Society Transactions 5:1739–1741.

Patel et al., 1977, "The Gastrointestinal Absorption of Liposomally Entrapped Insullin in Normal Rats", Biochemical Society Transactions 5:1054–1055.

Patel H.M., 1985, "Liposomes as a Controlled–Release System", Biochemical Society Transactions 13:513–516.

Patel et al., 1982, "Use of Liposomes to Aid Intestinal Absorption of Entrapped Insulin in Normal and Diabetic Dogs", Biochemica et Biophysica Acta 716:188–193.

Petkowicz, J. et al., 1989, "Hypoglycemic Effect of Liposome–Entrapped Insulin Administered By Various Routes into Normal Rats", Pol. J. Pharmacol. Pharm. 41(4):299–304.

Ryman, B.E. et al., 1978, "Potential Applications of Liposomes to Therapy", Ann. of the NY Acad. Sci. 308:281–307.

Scheen, A.J. et al., 1988, "Perspectives concernant les voies d'administration inhabituelles de l'insuline", Annales D. Endocrinologie 49(4–5):386–390.

Spangler, R.S., 1990 "Insulin Administration via Liposomes", Diabetes Care 13(9):911–922.

Tragl, K.H., et al., 1979, "Zur peroralen Verabreichung von Insulin mittels Liposomen im Tierversuch", Wiener Klinische Wochenschrift 91(13):448–451.

Tyminski, P.N. et al., 1985, "Rhodopsin in Polymerized Bilayer Membranes", J. Amer. Chem. Soc. 107:7769–7770.

Choi and Hahn, 1992, "Polymer–Coated Liposomes for Oral Drug Delivery", Yakche Hakhoechi 22:211–217 (Chem. Abstr. 118:407, Abstr. No. 197902e, 1993).

Okada et al., 1993, "Polymerized Liposomes for Oral Drug Delivery", Proc. Int. Symp. Controlled Release Bioact. Mater. pp. 302–303.

Patel et al., 1976, "Oral Administration of Insulin by Encapsulation within Liposomes", FEBS Lett. 62:60–63.

Regen, 1984, "Polymerized Vesicles", Polymer News 10:68–73.

Regen, 1987, "Polymerized Liposomes" *Liposomes: From Biophysics to Therapeutics* (Marcel Dekker, Inc., New York) pp. 73–109.

Skoza et al., 1978, "Procedure for Preparation of Liposomes with Large Internal Aqueous Space and High Capture by Reverse–phase Evaporation", Proc. Natl. Acad. Sci. USA 75:4194–4198.

Chen, 1996, *Polymerized Liposomes as Potential Oral Vaccine Delivery Vehicles*, (Doctoral Thesis, Massachusetts Institute of Technology).

Chen et al., 1996, "Polymerized Liposomes as Potential Oral Vaccine Carriers: Stability and Bioavailability", J. Controlled Release 42:263–272.

Chen et al., 1996, "Lectin–Bearing Polymerized Liposomes as Potential Oral Vaccine Carriers", Pharm. Res. 13:1378–1383.

Chen et al., 1996, "Surface–Modified Polymerized Liposomes: Novel Vehicles for Oral Vaccination", Proc. 5th World Congress of Chemical Engineering, pp. 824–829.

Ivanoff et al., 1996, "Mucosal Vaccination Against Schistosomiasis Using Liposome–Associated Sm 28 kDa Glutathione S–Transferase", Vaccine 14:1123–1131.

Chen et al., 1995, "Lectin–Bearing Polymerized Liposomes as Potential Oral Vaccine Carriers", Proc. Int. Symp. Controlled Release Bioact. Mater. 22:204–205 (CA: 123(26):350120y).

Chen and Langer, 1995, "Lectin–Bearing Polymerized Liposomes: Novel Vehicles for Oral Vaccine Delivery", Proc. 3rd U.S. –Japan Symposium on Drug Delivery, p. 23.

de Haan et al., 1995, "Mucosal Immunoadjuvant Activity of Liposomes: Induction of Systemic IgG and Secretory IgA Responses in Mice by Intranasal Immunization with an Influenza Subunit Vaccine and Coadministered Liposomes", Vaccine 13:155–162.

Estrada et al., 1995, "Intestinal Immunization of Mice with Antigen Conjugated to Anti–MHC Class II Antibodies", Vaccine 13:901–907.

Kilpatrick, 1995, "Lectins in Immunology", in:*Lectins: Biomedical Perspectives*, Pusztai and Bardocz, eds., Taylor & Francis, London, England, pp. 155–182.

Ogawa et al., 1995, "Oral Immunoadjuvant Activity of Lipophilic Derivatives of N–acetylglucosaminyl–β(1→4)–N–acetylmuramyl–L–alanyl–D–isoglutaminyl–(L)–2, 6–meso–diaminopimeric acid–(D)–amide", Vaccine 13:887–889.

Okada et al., 1995, "In Vitro Evaluation of Polymerized Liposomes as Oral Drug Delivery System", Pharm. Res. 12:576–582.

Zhou et al., 1995, "Mucosal IgA Response to Rectally Administered Antigen Formulated in IgA–Coated Liposomes", Vaccine 13:637–644.

Allen et al., 1994, "Antibody–Mediated Targeting of Long Circulating (Stealth®) Liposomes", J. Liposome Res. 4:1–25.

Anderson et al., 1994, "Cytokines in Liposomes: Preliminary Studies with IL–1, IL–2, IL–6, GM–CSF and Interferon–γ", Cytokine 6:92–101.

Aramaki et al., 1994, "Activation of Systemic and Mucosal Immune Response Following Nasal Administration of Liposomes", Vaccine 12:1241–1245.

Childers and Michalek, 1994, "Liposomes", pp. 241–254, in: *Novel Delivery Systems for Oral Vaccines*, O'Hagan, ed., CRC Press.

Lehr, 1994, "Bioadhesion Technologies for the Delivery of Peptide and Protein Drugs to the Gastrointestinal Tract", Critical Reviews in Therapeutic Drug Carrier Systems 11:119–160.

Lipford et al., 1994, "Vaccination with Immunodominant Peptides Encapsulated in Quil A–Containing Liposomes Induces Peptide-Specific Primary CD8+ Cytotoxic T Cells", Vaccine 12:73–80.

O'Hagan, 1994, "Microparticles as Oral Vaccines", in: *Novel Delivery Systems for Oral Vaccines*, O'Hagan, ed., CRC Press, Boca Raton, FL, pp. 175–204.

Russel–Jones, 1994, "Oral Vaccination with Lectins and Lectin–Like Molecules", in: *Novel Delivery Systems for Oral Vaccines*, O'Hagan, ed., CRC Press, Boca Raton, FL, pp. 225–254.

Tanguay et al., 1994, "In Vivo Modulation of Macrophage Tumoricidal Activity by Oral Administration of the Liposome–Encapsulated Macrophage Activator CGP 19835A", Cancer Res. 54:5882–5888.

Aramaki et al., 1993, "Stability of Liposomes In Vitro and Their Uptake by Rat Peyer's Patches Following Oral Administration", Pharm. Res. 10: 1228–1231.

Clarke and Stokes, 1992, "The Intestinal and Serum Humoral Immune Response of Mice to Systemically and Orally Administered Antigens in Liposomes: I. The Response to Liposome–Entrapped Soluble Proteins", Vet. Immunol. Immunopathol. 32:125–138.

Clarke and Stokes, 1992, "The Intestinal and Serum Humoral Immune Response of Mice to Orally Administered Antigens in Liposomes: II. The Response to Liposome–Entrapped Bacterial Proteins", Vet. Immunol. Immunopathol. 32:139–148.

Tsuchida et al., 1992, "Polymerization of Unsaturated Phospholipids as Large Unilamellar Liposomes at Low Temperature", Macromolecules 25:207–212.

Uwiera et al., 1992, "Liposomes Targeted to Deliver Antisecretory Agents to Jejunal Mucosa", Can. J. Vet. Res. 56:249–255.

Childers et al., 1990/1991, "Mucosal and Systemic Responses to an Oral Liposome *Streptococcus mutans* Carbohydrate Vaccine in Humans", Regional Immunol. 3:289–296.

Childers, et al., 1990, "Ultrastructural Study of Liposome Uptake by M Cells of Rat Peyer's Patch: An Oral Vaccine System for Delivery of Purified Antigen", Regional Immunol. 3;8–16.

Eldridge et al., 1990, "Controlled Vaccine Release in the Gut–Associated Lymphoid Tissues. I. Orally Administered Biodegradable Microspheres Target the Peyer's Patches", J. Controlled Release 11:205–214.

Gregoriadis, 1990, "Immunological Adjuvants: A Role for Liposomes", Immunol. Today 11:89–97.

Michalek et al., 1989, "Liposomes as Oral Adjuvants", Curr. Topics in Microbiol. and Immunol. 146:51–58.

Freeman and Chapman, 1988, "Polymerizable Liposomes: Applications in Biology and Medicine", in: *Liposomes as Drug Carriers* Gregoriadis, ed., John Wiley & Sons, pp. 821–839.

Kimura, 1988, "Transmucosal Passage of Liposomal Drugs", in: *Liposomes as Drug Carriers* Gregoriadis, ed., John Wiley & Sons, pp. 635–647.

Barbour et al., 1987, "Protection and Immunity in Commercial Chicken Layers Administered *Mycoplasma gallisepticum* Liposomal Bacterins", Avian Diseases 31:723–729.

Neutra et al., 1987, "Transport of Membrane–Bound Macromolecules by M Cells in Follicle–Associated Epithelium of Rabbit Peyer's Patch", Cell Tissue Res. 247:537–546.

Ogawa et al., 1986, "Enhancement of Serum Antibody Production in Mice by Oral Administration of Lipophilic Derivatives of Muramylpeptides and Bacterial Lipopolysaccharides with Bovine Serum Albumin", Meth.and Find. Exptl. Clin. Pharmacol. 8:117–125.

Weissig et al., 1986, "A New Hydrophobic Anchor for the Attachment of Proteins to Liposomal Membranes", FEBS Lett. 202:86–90.

O'Connor et al., 1985, "Bile Salt Damage of Egg Phosphatidylcholine Liposomes", Biochim. Biophys. Acta 817:95–102.

Regen, 1985, "Polymerized Phosphatidylcholine Vesicles as Drug Carriers", Ann. N.Y. Acad. Sci. 446:296–307.

Woodley, 1985, "Liposomes for Oral Administration of Drugs", CRC Crit. Rev. in Therapeutic Drug Carrier Systems 2:1–18.

Dorn et al., 1984, "Permeability Characteristics of Polymeric Bilayer Membranes from Methacryloyl and Butadiene Lipids", J. Am. Chem. Soc. 106:1627–1633.

Deshmukh et al., 1981, "Can Intact Liposomes Be Absorbed in the Gut?", Life Sci. 28:239–242.

Gros et al., 1981, "Polymeric Antitumor Agents on a Molecular and on a Cellular Level?", Angew. Chem. Int. Ed. Engl. 20:305–325.

Hupfer et al., 1981, "Polyreactions in Oriented Systems, 21; Polymeric Phospholipid Monolayers", Makromol. Chem. 182:247–253.

Weingarten et al., 1981, "Oral Ingestion of Insulin Liposomes: Effects of the Administration Route", Life Sci. 28:2747–2752.

Regen et al., 1980, "Polymerized Vesicles", J. Am. Chem. Soc. 102:6638–6640.

Rowland and Woodley, 1980, "The Stability of Liposomes In Vitro to pH, Bile Salts and Pancreatic Lipase", Biochim. Biophys. Acta 620:400–409.

ORAL DELIVERY OF VACCINES USING POLYMERIZED LIPOSOMES

This is a continuation of application Ser. No. 08/096,689, filed Jul. 23, 1993, now abn.

This invention relates to the synthesis, preparation, and use of polymerized liposomes as sustained drug and/or antigen release devices.

BACKGROUND OF THE INVENTION

Drug delivery takes a variety of forms, depending on the agent to be delivered and the administration route. The most convenient way to administer drugs into the body is by oral administration. However, many drugs, in particular proteins and peptides, are poorly absorbed and unstable during passage through the gastrointestinal (G-I) tract. The administration of these drugs is generally performed through parenteral injection.

Although oral vaccination is more convenient, vaccines are generally given through injection. This is particularly true with killed or peptidic vaccines, because of their low absorbability and instability in the G-I tract. A problem with systemic immunization is that it may not effectively induce mucosal immune responses, particularly production of IgA, that are important as the first defense barrier to invaded microorganisms. For this reason, it would be beneficial to provide oral vaccination, if the problems of low absorbability and instability could be overcome.

Controlled release systems for drug delivery are often designed to administer drugs to specific areas of the body. In the gastrointestinal tract it is important the drug not be eliminated before it has had a chance to exert a localized effect or to pass into the bloodstream.

Enteric coated formulations have been widely used for many years to protect drugs administered orally, as well as to delay release. Several microsphere formulations have been proposed as a means for oral drug delivery. For example, PCT/US90/06430 and PCT/US90/06433 by Enzytech discloses the use of a hydrophobic protein, such as zein, to form microparticles; U.S. Pat. No. 4,976,968 to Steiner, et al. discloses the use of "proteinoids" to form microparticles; and European Patent Application 0,333,523 by The UAB Research Foundation and Southern Research Institute discloses the use of synthetic polymers such as polylactic acid-glycolic acid to form microspheres.

Particles less than ten microns in diameter, such as the microparticles of EPA 0,333,523, can be taken up by cells in specialized areas, such as Peyer's patches and other intestinal mucosal lymphoid aggregates, located in the intestine, especially in the ileum, into the lymphatic circulation. Entrapping a drug or antigen in a microparticulate system can protect the drug or antigen from acidic and enzymatic degradation, yet still allow the drug or antigen to be administered orally, where they are taken up by the specialized uptake systems, and release the entrapped material in a sustained manner or are processed by phagocytic cells such as macrophages. When the entrapped material is a drug, elimination of the first-pass effect (metabolism by the liver) is highly advantageous.

Liposomes have been proposed for use as an oral drug delivery system, for example, by Patel and Ryman, *FEBS Letters* 62(1), 60–63 (1976). Liposomes are typically less than 10 microns in diameter, and, if they were stable to passage through the GI tract, should be absorbed through the Peyer's patches. Liposomes also have some features that should be advantageous for a particulate system for oral drug or antigen delivery. The phospholipid bilayer membrane of liposomes separates and protects entrapped materials in the inner aqueous core from the outside. Both water-soluble and -insoluble substances can be entrapped in different compartments, the aqueous core and bilayer membrane, respectively, of the same liposome. Chemical and physical interaction of these substances can be eliminated because the substances are in these different compartments. Further, liposomes are easy to prepare. However, liposomes are physically and chemically unstable, and rapidly leak entrapped material and degrade the vesicle structure. Without fortifying the liposomes, they are not good candidates for oral drug or antigen delivery.

Several methods have been tried to fortify liposomes. Some methods involved intercalating cholesterol into the bilayer membrane or coating the liposome with polysaccharides. These methods are not useful in making liposome for oral delivery since during oral delivery liposomes are exposed to an acidic pH in the stomach and bile salts and phospholipases in intestine. These conditions break down the cholesterol and polysaccharide in the liposomes.

There remains a need for drug and antigen delivery devices that can survive the harsh conditions in the GI tract, and yet effectively deliver the drug and antigen.

It is therefore an object of the invention to provide stable liposomes for use in oral drug and antigen delivery.

It is a further object of the invention to provide methods of preparing stabilized liposomes.

It is still a further object of the invention to provide a method for orally administering drugs or antigens entrapped within these stabilized liposomes to a patient in need of the drug or antigen.

SUMMARY OF THE INVENTION

Polymerized liposomes are disclosed which are useful in oral delivery of compounds. The constituent phospholipids and/or the leaflets are polymerized by covalent bonding to each other. Covalently binding the layers adds strength, resulting in a less fluid unpolymerized liposome. The less fluid bi-layer membrane suppresses leakage. Further, the detergent-like bile salts in the intestine cannot extract the phospholipid molecules. These cross-linked membranes are strong enough to maintain their structure even if the phospholipids undergo hydrolysis at low pH and enzymatic degradation by phospholipases. Polymerized liposomes reach the ileum of the GI tract as intact particulates, and are absorbed.

Polymerized liposomes are prepared by polymerizing double bond-containing olefinic and acetylenic phospholipids. In addition, polymerized liposomes can be prepared by chemical oxidation of thiol groups in the phospholipids to disulfide linkages. The polymerization can take place in a solution containing a biologically active substance, such as a drug or antigen, in which case the substance is encapsulated during the polymerization. Alternatively, the liposomes can be polymerized first, and the biologically active substance can be added later by resuspending the polymerized liposomes in a solution of a biologically active substance, and entrapping the substance by sonication of the suspension. Another method of entrapping a biologically active substance in polymerized liposomes is to dry the polymerized liposomes to form a film, and hydrate the film in a solution of the biologically active substance. The above conditions are typically mild enough to entrap biologically active substances without denaturing them.

DETAILED DESCRIPTION OF THE INVENTION

The polymerized liposomes, methods of preparing these liposomes, and methods of using these polymerized liposomes for controlled drug delivery are disclosed herein.
Definitions As used herein, the term "liposome" is defined as an aqueous compartment enclosed by a lipid bilayer. (Stryer, *Biochemistry*, 2d Edition, W. H. Freeman & Co., p. 213 (1981). The liposomes can be prepared by a thin film hydration technique followed by a few freeze-thaw cycles. Liposomal suspensions can also be prepared according to methods known to those skilled in the art, for example, as described in U.S. Pat. No. 4,522,811, incorporated herein by reference in its entirety.

As used herein, the term "polymerized liposome" is defined as a liposome in which the constituent phospholipids are covalently bonded to each. The phospholipids can be bound together within a single layer of the phospholipid bilayer (the leaflets) and/or bound together between the two layers of the bilayer.

The degree of crosslinking in the polymerized liposomes can range from 30 to 100 percent, i.e., up to 100 percent of the available bonds are made. The size range of polymerized liposomes is between approximately 15 nm to 10 μm. The polymerized liposomes can be loaded with up to 100% of the material to be delivered, when the material is hydrophobic and attracted by the phospholipid layers. In general, five to 40 percent of the material is encapsulated when the material is hydrophilic.

As used herein, the term "trap ratio" is defined as the ratio of inner aqueous phase volume to total aqueous phase volume used.

As used herein, the term "radical initiator" is defined as a chemical which initiates free-radical polymerization.

As used herein, the term "reverse phase evaporation technique" is defined as a method involving dissolving a lipid in an organic solvent, adding a buffer solution, and evaporating the organic solvent at reduced pressure, as described by Skoza, F. Jr., and Papahadjopoulos, D., *Proc. Natl. Acad. Sci. USA*, Volume 75, No. 9, pp. 4194–4198 (1978).

As used herein, the term "freeze-thaw technique," or "F-T," is defined as freezing a suspension in liquid nitrogen, and subsequently thawing the suspension in a roughly 30° C. water bath.

As used herein, the term "buffer solution" is defined as an aqueous solution or aqueous solution containing less than 25% of a miscible organic solvent, in which a buffer has been added to control the pH of the solution. Examples of suitable buffers include but are not limited to PBS (phosphate buffered saline), TRIS (tris(hydroxymethyl) aminomethane), HEPES (hydroxyethylpiperidine ethane sulfonic acid), and TES 2-[(tris-hydroxymethyl)methyl] amino-1-ethanesulfonic acid.

As used herein, the term "leaflets" is defined as a single layer of phospholipid in the bilayer forming the liposome.
Preparation of Polymerized Phospholipid The polymerized liposomes are generally prepared by polymerization of double bond-containing monomeric phospholipids. These phospholipids must contain at least polymerizable functional group double bonds, but may contain more than one polymerizable functional group double bond. Examples of polymerizable functional groups include but are not limited to olefins, acetylenes, and thiols. Suitable monomeric phospholipids include but are not limited to DODPC (1,2-di(2,4-Octadecadienoyl)-3-phosphatidylcholine). If the liposome is polymerized by oxidation of thiol groups, it is preferred not to encapsulate thiol-containing biologically active substances, as they could be oxidized during the polymerization step.
Polymerization by Free Radical Initiation The monomeric double bond-containing phospholipids can be polymerized using a hydrophobic free radical initiator, such as AIBN (azo-bis-isobutyronitrile), or a hydrophilic free radical initiator such as AIPD (azo-bis-amidinopropane dihydrochloride). The latter is particularly useful for initiating polymerization between layers of the bilayer. Alternatively, polymerization can be initiated by using a radiation source, such as ultraviolet or gamma radiation. Use of the free radical initiators is preferred if the biologically active substance to be entrapped is denatured when exposed to radiation.

The ratio between the phospholipid and crosslinker and aqueous phase all affect the percent of crosslinking. In general, the percent crosslinking increases as the amount of crosslinker or time or temperature of reaction are increased. As the percent crosslinking increases, the release rate of the materials from the liposomes decreases and the stability increases.
Polymerization by Radiation If the biologically active substance to be incorporated cannot tolerate these temperatures, one can initiate the polymerization with ultraviolet and or gamma radiation, provided the biologically active substance can survive exposure to the radiation. Typical conditions for initiating the polymerization with ultraviolet radiation include but are not limited to irradiating the solution at 254 nm, 100 W, for 3 hours at room temperature. Typical conditions for initiating the polymerization with gamma radiation include but are not limited to irradiating the solution at 0.3 mRad per hour for 3 hours at room temperature.

Encapsulation of Biologically Active Material

Materials are generally incorporated into the liposomes at the time of formation, following polymerization using sonication of a solution of the material which contains the liposomes, and following polymerization by rehydration of a thin film of the liposomes.

The following is a general method for the preparation of polymerized liposomes wherein a biologically active substance is entrapped prior to the polymerization of the monomeric double bond-containing liposome. First, the monomeric liposome is prepared by the thin film hydration of a monomeric double bond-containing phospholipid. The monomeric phospholipid is dissolved, and the solution is then dried to form a thin film of phospholipid. A solution containing substance to be entrapped is added, preferably with a catalytic amount (1–3 percent by weight) of free radical initiator. At this stage, it is preferable to establish an inert atmosphere. The lipid film is then hydrated by gently shaking and sonicating the solution at a temperature of from 30° to 50° C., usually around 40° C., for between five minutes and two hours, preferably around five minutes. Once the lipid film is hydrated, the trap ratio of the liposome can be increased by performing one or more freeze-thaw cycles on the liposome solution. This is particularly useful when the material being incorporated is hydrophilic in nature. Next, the polymerization is carried out at an elevated temperature, from 60° to 100° C., preferably at around 60° C., for 5 to 20 hours, preferably about 5 hours, or until the polymerization is essentially complete. The desired degree of crosslinking is from 30 to 100 percent.

Unentrapped biologically active substance can be removed by several means, including repeated centrifugation, decantation, gel filtration, and dialysis. The polymerized liposomes are then suspended in a buffer solution. The buffer solution has a pH preferably between pH 4.5 and pH 9.5, more preferably at physiological pH.

This method of entrapping biologically active substances is preferred because it does not involve the use of organic solvents. Use of organic solvents can denature biologically active substances. Further, the temperature requirements are mild, with the temperature typically not exceeding 60° C.

If the biologically active substance cannot tolerate the temperature conditions or exposure to radiation, a third method of entrapping the substance in a polymerized liposome is preferred. In this method, the liposomes are polymerized before adding the material to be encapsulated. After the polymerization is complete, the polymerized liposomes are added to an aqueous solution of the material. The solution should be aqueous, although it can include small amounts of organic solvent. The solution is sonicated, and the sonication entraps the substance inside the polymerized liposome.

Another method for entrapping biologically active substances in polymerized liposomes is to dissolve the polymerized liposomes in a suitable organic solvent, such as tetrahydrofuran, acetone, ether, chloroform, methylene dichloride, and ethyl acetate, and evaporate the solvent to form a thin film of polymerized liposome. Hydrophobic materials are preferably encapsulated in the liposomes by dissolving the materials in an organic solvent with the phospholipid, before forming the liposomes. Hydrophilic materials are more preferably incorporated by hydrating a thin film of polymerized liposomes in the presence of an aqueous solution of the substance.

Materials can be entrapped within the liposomes, as well as or alternatively in one or more of the lipid layers of the phospholipid bilayer. This is typically determined by the hydrophobicity/hydrophilicity of the material to be incorporated as well as the method of preparation.

Materials to be Incorporated

As used herein, the term "biologically active substance" refers to eukaryotic and procaryotic cells, viruses, vectors, proteins, peptides, nucleic acids, polysaccharides and carbohydrates, lipids, glycoproteins, and combinations thereof, and synthetic organic and inorganic drugs exerting a biological effect when administered to an animal. For ease of reference, this term is also used to include detectable compounds such as radiopaque compounds including air and barium, magnetic compounds, fluorescent compounds, and radioactive compounds. The active substance can be soluble or insoluble in water. Examples of biologically active substances include anti-angiogenesis factors, antibodies, antigens, growth factors, hormones, enzymes, and drugs such as steroids, anti-cancer drugs or antibiotics, as well as materials for use as insecticides or insect repellents, fertilizers and vitamins, or any other material having a biological effect where controlled release is desirable.

In a diagnostic embodiment, the polymerized liposome incorporates a pharmaceutically acceptable gamma-emitting moiety, including but not limited to, indium and technectium, magnetic particles, radioopaque materials such as air or barium and fluorescent compounds.

As used herein, the term "ligand" refers to a ligand attached to the polymerized liposomes which adheres to the mucosa in the intestine or can be used to target the liposomes to a specific cell type in the GI tract or following absorption. These can range from ligands for specific cell surface proteins and antibodies or antibody fragments immunoreactive with specific surface molecules, to less specific targeting such as coatings of materials which are bioadhesive, such as alginate and polyacrylate. In general, ligands are bound to or inserted within the polymerized phospholipids; adhesive polymers are applied as a coating to the particles.

As noted above, the liposomes can be modified by attaching to the surface of the particle specific ligands for given cells in a mixture of cells. When magnetic particles are also incorporated, the particles can be targeted using the ligands, such as tissue specific receptors or antibodies to tissue specific surface proteins, then maintained at the targeted cells using a magnetic field while the particles are imaged or a compound to be delivered is released.

Orally delivered biologically active substances, like food, are generally excreted within two or three days after delivery. However, the polymerized lipospheres can be retained longer if the liposomes are made more "bioadhesive" by attachment of various bioadhesive ligands to the liposomes. These bioadhesive polymerizable liposomes are advantageous over conventional liposomes, and even over polymerized liposomes that lack bioadhesive ligands. Bioadhesive ligands include attachment peptides such as RGD, and extracellular matrix materials such as fibronectin.

Modes of Administering the Polymerized Liposomes to a Patient

The polymerized liposomes are preferably orally administered to a patient, although they can be administered topically or by injection (parenterally). They can also be administered in a capsule. When the dosage unit form is a capsule, it can contain, in addition to, material of the above type, a liquid carrier or adjuvant, when the liposomes contain an antigen. If administered topically the liposomes will typically be administered in the form of an ointment or transdermal patch.

The present invention will be further understood by reference to the following non-limiting examples.

EXAMPLE 1

Preparation of Polymerized Liposomes

In a typical preparation, 80 mg of the polymerizable phospholipid, 1,2-di(2,4-Octadecadienoyl)-3-phosphatidylcholine (DODPC), 1.68 mg of Azo-bis-isobutyronitrile (AIBN) as a radical initiator, and lipid A derivative as an adjuvant were dissolved in 4 mL chloroform. The solution was dried in vacuo to form a thin film on the inside wall of a round bottom flask. A vaccine solution (1 mL of a 1 mg/mL solution) containing 2.68 mg of Azo-bis-(amidinopropane) dihydrochloride (AAPD) as another radical initiator was added to the flask. A nitrogen atmosphere was established and the flask was sealed. The lipid film was gradually hydrated by gently shaking the flask at 40° C. for 5 minutes, followed by tip-sonication (10 W for 10 seconds). To increase the trap ratio, the liposome suspension was subjected to three freeze-thaw cycles, by freezing the suspension in liquid nitrogen and then thawing the suspension in a 30° C. water bath. The liposome suspension was polymerized at 60° C. for 5 hours, at which time polymerization was completed. Polymerization was considered complete when 95% of the double or triple bonds are crosslinked. Unentrapped vaccine antigen was removed by repeated centrifugation cycles and addition of fresh buffer. Finally, the polymerized liposomes were suspended in the appropriate buffer solution.

The liposomes were in the size range of 4±2 μm diameter as measured by a Coulter Counter particle sizer. The trap ratio of vaccine solution in polymerized liposomes (35%) was similar to that of pre-polymerized liposome preparations. The trap ratio of 35% is comparable to that of liposomes prepared by other techniques such as the "reverse phase evaporation technique". Further, the water insoluble adjuvant was embedded in the liposome membrane practically without any loss during the preparation process.

The inside structure of each liposome was drastically changed following the freeze-thaw (F-T) treatment, as determined by freeze-fracture electron microscopy. Originally, the liposomes had multi-layered structures and a small volume of inside aqueous phase. The freeze-thaw treatment reduced the number of layers and increased the volume of inner aqueous phase. Additionally, freeze-thaw treatment equilibrated the concentration of solute in the aqueous phase inside and outside of the liposomes. As a result, the trap ratio increased from a few % to around 35%.

The concentration of entrapped material in the final liposome suspension can be controlled by the original concentration of the material to be entrapped in the aqueous phase used for preparation, and the volume of continuous aqueous phase in which liposomes are suspended.

EXAMPLE 2

In Vitro Release of Entrapped Material $^{14}$C labelled bovine serum albumin (BSA) was used as a model protein to follow the in vitro release profiles of the material incorporated in liposomes. The polymerized liposomes containing $^{14}$C labelled BSA were prepared as described in Example 1. Additionally, non-polymerized liposomes of the same phospholipid composition (DODPC) and of hydrogenated egg phosphatidylcholine and cholesterol (molar ratio 1:1) were prepared as controls by the same procedure but were not polymerized. The particle sizes and trap ratios of the reference samples were similar to those of the polymerized liposomes.

Release studies were conducted in 1) pH 7.4 isotonic Tris buffered saline, 2) pH 2.0 isotonic HCl saline, and 3) pH 7.4 isotonic Tris saline containing 20 mM sodium taurocholate, 5 U/mL phospholipase $A_2$, and 2 mM $CaCl_2$. The latter two media simulate physiological conditions in the stomach and the intestine fluid, respectively.

Figure 1:
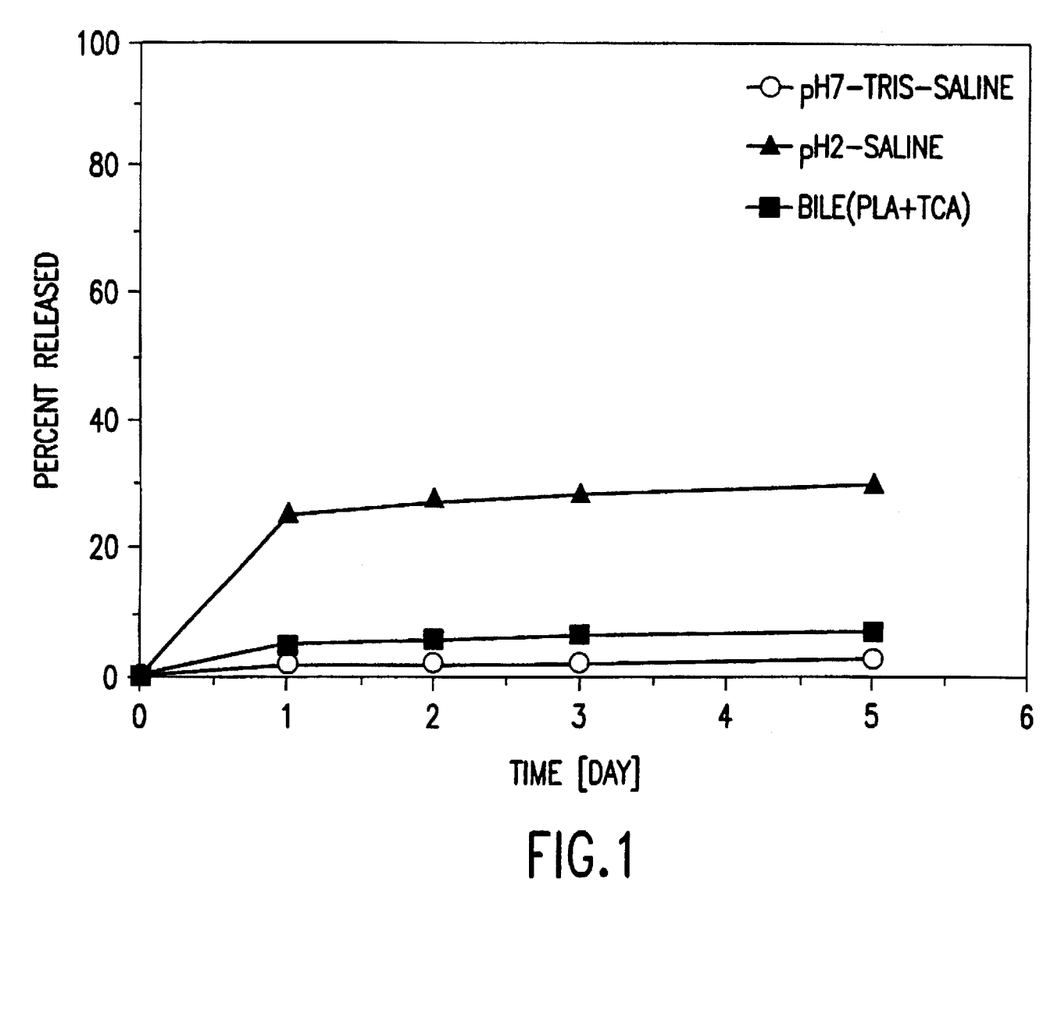
FIG. 1 is a graph of the percent BSA (Bovine Serum Albumin) released from polymerized liposomes of DODPC (1,2-di(2,4-Octadecadienoyl)-3-phosphatidylcholine), in various solvent systems, as a function of time (in days). The open circles represent release of BSA in a solution buffered to pH 7 with Tris-saline. The darkened triangles represent the release of BSA in a solution of pH 2 saline. The darkened squares represent the release of BSA in a solution of bile (PLA and TCA).
Figure 2:
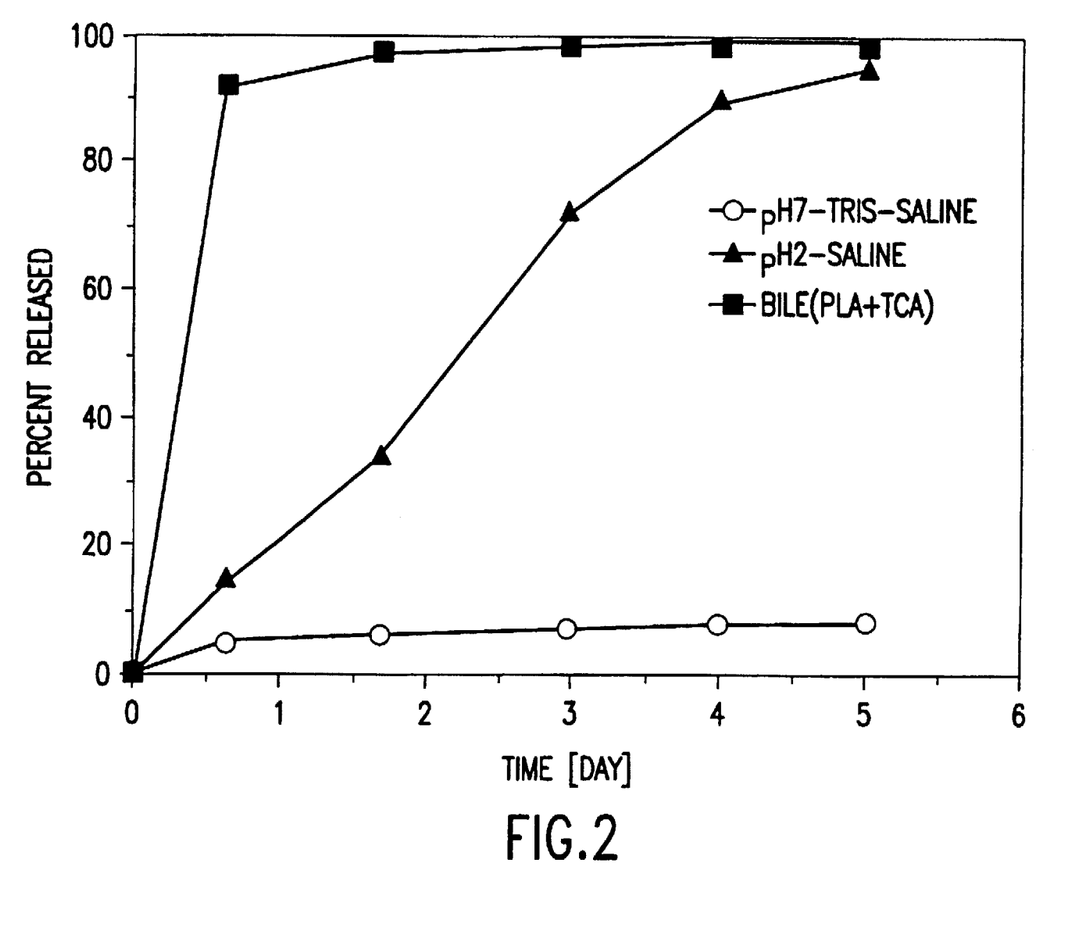
FIG. 2 is a graph of the percent BSA (Bovine Serum Albumin) released from unpolymerized liposomes of DODPC (1,2-di(2,4-Octadecadienoyl)-3-phosphatidylcholine), in various solvent systems, as a function of time (in days). The open circles represent release of BSA in a solution buffered to pH 7 with Tris-saline. The darkened triangles represent the release of BSA in a solution of pH 2 saline. The darkened squares represent the release of BSA in a solution of bile (PLA and TCA).
Figure 3:
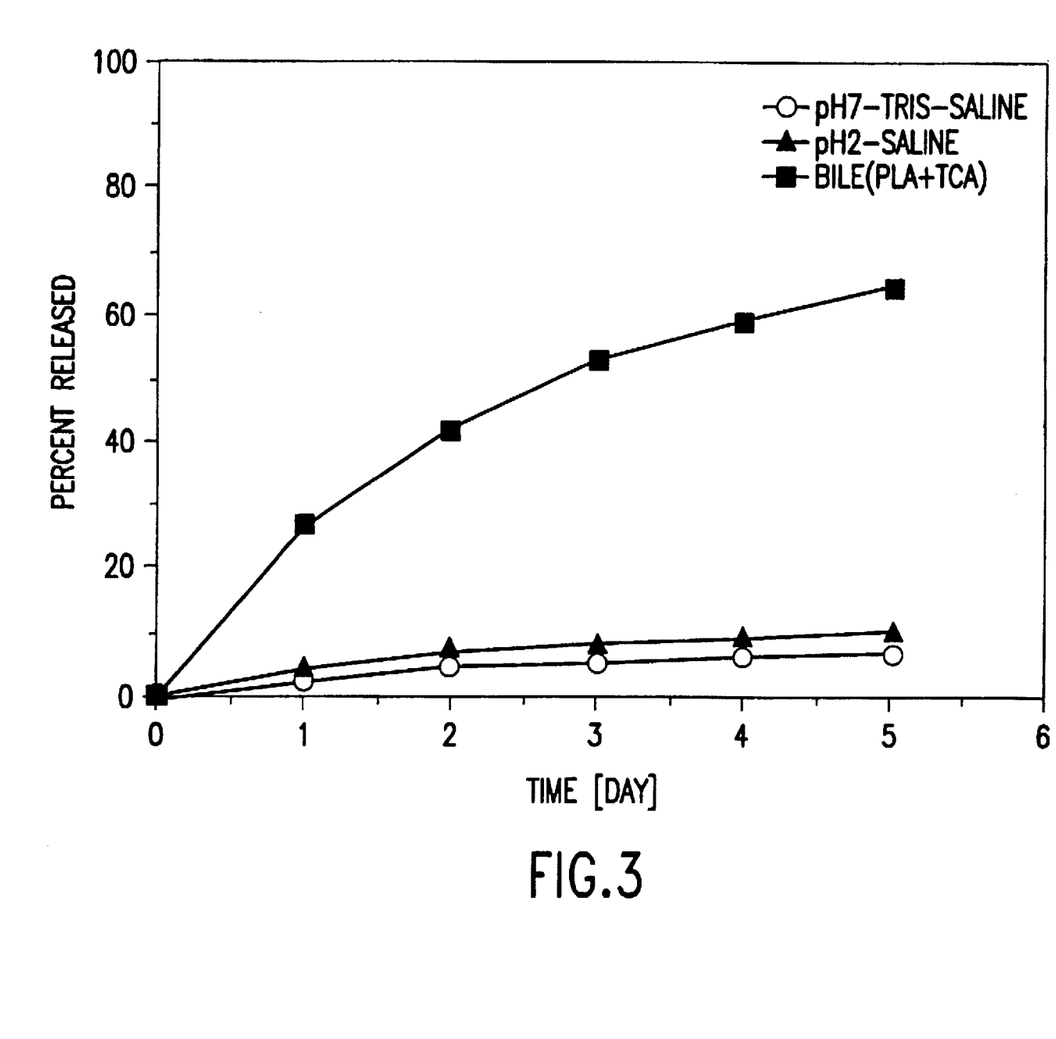
FIG. 3 is a graph of the percent BSA (Bovine Serum Albumin) released from liposomes of hydrogenated egg phosphatidylcholine and cholesterol, in various solvent systems, as a function of time (in days). The open circles represent release of BSA in a solution buffered to pH 7 with Tris-saline. The darkened triangles represent the release of BSA in a solution of pH 2 saline. The darkened squares represent the release of BSA in a solution of bile (PLA and TCA).

The results of release studies are shown in FIGS. 1, 2 and 3. FIG. 1 displays slow release rates of protein from polymerized liposomes. In acidic solution, less than 5% was released after 6 hours incubation in acidic medium. This would generally be the longest retention time of the liposomes in the stomach, and indicates the polymerized liposomes are stable to acid pH during transit through the stomach. In intestinal-simulated media, there was less than 5% release even after 5 days. These conditions, in general, destabilize liposomes. FIG. 2 shows faster release rates from non-polymerized liposomes, of about 90% after 1 day in the intestinal-simulated medium.

The bi-layers in the polymerized liposomes are stabilized by polymerizing the phospholipids. This stabilization is likely the cause of the slower release in the polymerized liposomes relative to the unpolymerized liposomes. FIG. 3 shows protein release patterns from hydrogenated egg phosphatidyl choline (PC) liposomes containing cholesterol. Although this liposome preparation is considered the most stable among conventional liposomes, it shows faster release rates in the intestinal-simulated media (about 30% after 5 days) than polymerized liposomes.

EXAMPLE 3

Measurement of the Absorption of Biologically Active Substances Entrapped in Polymerized Liposomes Polymerized liposomes containing $^{125}$I-BSA were orally administered to rats. The absorption of 125I-BSA into the blood was then examined. $^{125}$I-BSA containing monomeric liposomes and $^{125}$I-BSA solution were used as controls. The polymerized liposomes were prepared as described in Example 1. Monomeric liposomes were made of hydrogenated egg phosphatidylcholine and cholesterol (1:1 molar ratio).

Figure 4:
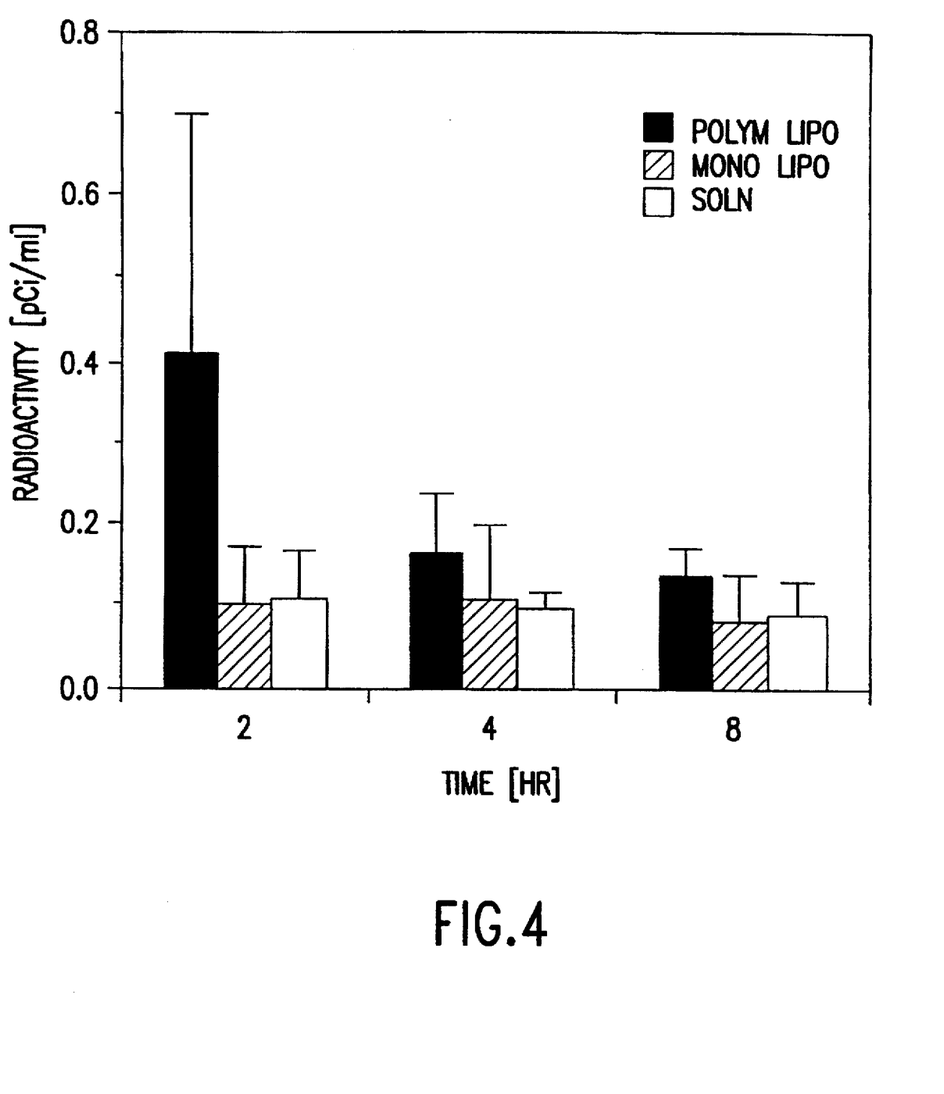
FIG. 4 is a graph of the total absorption of radioactive protein (in picocuries) as a function of time (in hours). The darkened bars represent the absorption of protein from polymerized liposomes. The hashed bars represent the absorption of protein from unpolymerized liposomes. The white bars represent the absorption of protein from a protein solution.

Each formulation, including the control $^{125}$I-BSA solution, was administered intragastrically with ball-tipped needle and blood was sampled at appropriate intervals from the tail vein. To distinguish between transport of $^{125}$I-BSA in the context of liposomes, free $^{125}$I-BSA, and the radiolabelled degradation product of $^{125}$I-BSA, the blood samples were separated into three fractions: 1) cell debris fraction, 2) trichloroacetic acid (TCA) precipitable fraction, and 3) TCA non-precipitable fraction. FIG. 4 shows the sum of the radioactivities belonging to the fractions 1) and 2) in the blood of rats to which each dosage form was administered orally.

The results show that the "effective uptake" is much more from polymerized liposomes administration. Feces of rats were homogenated with water and centrifuged to separate solid stuff. Radioactivity in the whole homogenate and sedimented solid were compared. In the case of polymerized liposome administered rats, almost 80% of total radioactivity was observed in the solid, compared with only 10% from monomeric liposome administered rats. This result suggests that polymerized liposomes are so stable in the GI tract that the liposomes of this formulation remain as intact structures until excreted.

Because the elimination of the precipitable fraction in blood after intravenous injection was slow, i.e., 75% remaining at 6 hours after injection, the TCA non-precipitable fraction was smaller in animals administered material in polymerized liposomes, as compared to material administered in conventional liposomes and significantly less than when material was administered in solution.

Variations and modifications of the compositions, methods of preparing the compositions, and methods of using the compositions will be obvious to those with ordinary skill in the art. It is intended that all of these variations and modifications be included within the scope of the appended claims.

We claim:

1. A method of delivering an antigen to the gastrointestinal tract of an animal which comprises orally administering to said animal polymerized liposomes comprising a phospholipid bilayer having covalently bonded phospholipids therein, an aqueous core and an antigen encapsulated in said polymerized liposome.

2. A method of orally delivering a vaccine to the gastrointestinal tract of an animal which comprises orally administering to said animal polymerized liposomes comprising a phospholipid bilayer having covalently bonded phospholipids therein, an aqueous core and a vaccine encapsulated in said polymerized liposome.

3. The method of claim 2 wherein said polymerized liposome further comprises a detectable material selected from the group consisting of radiopaque substances, radioactive substances, fluorescent substances, air, magnetic materials, and substances detectable by magnetic resonance imaging.

4. The method of claim 3 further comprising detecting the compound after administration to the animal.

5. The method of claim 2 wherein said vaccine is an antigen and said polymerized liposomes are administered in an amount effective to elicit a humoral, secretory or cell mediated immune response against the antigen.

6. The method of claim 2 wherein said polymerized liposome further comprises an adjuvant.

7. The method of claim 2 wherein said vaccine is selected from the group consisting of viruses, proteins, glycoproteins, nucleic acids, carbohydrates, and lipids.

8. The method of claim 2 wherein said vaccine is selected from the group consisting of peptides, vectors, monosaccharides and polysaccharides.

9. The method of claim 2 wherein said vaccine is an antibody.

10. The method of claim 1 or 2 wherein said polymerized liposome further comprises a targeting molecule selected from the group consisting of antibodies, antibody fragments, antigens and molecules capable of binding to specific cell surface receptors found in the mucosal tissue.

11. The method of claim 1 or 2 wherein said animal is a human.

12. The method of claim 1 or 2 wherein said covalently bonded phospholipid is selected from the group consisting of olefinic or double bond-containing phospholipids, acetylenic phospholipids and phospholipids containing thiol groups.

13. The method of claim 12 wherein said covalently bonded phospholipid bilayer comprises DODPC.

* * * * *